(12) United States Patent
Wu et al.

(10) Patent No.: US 7,881,435 B2
(45) Date of Patent: Feb. 1, 2011

(54) DETECTOR PANEL AND X-RAY IMAGING APPARATUS

(75) Inventors: Zhu Wu, Beijing (CN); Michael J. Utschig, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 90 days.

(21) Appl. No.: 12/358,898

(22) Filed: Jan. 23, 2009

(65) Prior Publication Data

US 2009/0202038 A1 Aug. 13, 2009

(30) Foreign Application Priority Data

Feb. 13, 2008 (CN) .................. 2008 1 0074226

(51) Int. Cl.
*H05G 1/64* (2006.01)
(52) U.S. Cl. .................. 378/98.8; 378/189; 250/370.09
(58) Field of Classification Search .................. 378/19, 378/98.8, 189, 198; 250/370.09
See application file for complete search history.

(56) References Cited

U.S. PATENT DOCUMENTS

| | | | |
|---|---|---|---|
| 4,681,227 A | 7/1987 | Tamura et al. | |
| 4,922,105 A | 5/1990 | Hosoi | |
| 5,081,543 A | 1/1992 | Romandi | |
| 5,514,873 A | 5/1996 | Schulze-Ganzlin et al. | |
| 5,804,832 A * | 9/1998 | Crowell et al. | 250/580 |
| 5,877,501 A | 3/1999 | Ivan et al. | |
| 5,912,941 A | 6/1999 | Schmitt | |
| 6,091,982 A | 7/2000 | Reinke et al. | |
| 6,205,119 B1 | 3/2001 | Kaczynski | |
| 6,575,624 B2 | 6/2003 | Noegel et al. | |
| 6,700,126 B2 | 3/2004 | Watanabe | |
| 6,825,472 B2 * | 11/2004 | Endo | 250/370.09 |
| 7,016,467 B2 * | 3/2006 | Brooks | 378/102 |
| 7,057,181 B2 * | 6/2006 | Yagi | 250/370.09 |
| 7,078,703 B2 | 7/2006 | Watanabe | |
| 7,104,686 B2 * | 9/2006 | Watanabe et al. | 378/189 |
| 7,164,137 B2 | 1/2007 | Hayashida | |
| 7,189,972 B2 | 3/2007 | Ertel et al. | |
| 7,202,481 B2 * | 4/2007 | Spahn et al. | 250/370.09 |
| 7,317,190 B2 | 1/2008 | Ertel et al. | |
| 7,342,998 B2 | 3/2008 | Kump et al. | |
| 7,396,159 B2 | 7/2008 | Utschig et al. | |
| 7,429,737 B2 * | 9/2008 | Wojcik et al. | 250/370.09 |
| 7,435,967 B2 | 10/2008 | Ertel et al. | |
| 7,488,946 B2 * | 2/2009 | Hennessy et al. | 250/370.09 |
| 7,495,226 B2 * | 2/2009 | Jadrich et al. | 250/370.09 |
| 7,569,831 B2 * | 8/2009 | Jadrich et al. | 250/370.11 |
| 7,581,883 B2 * | 9/2009 | Kato | 378/167 |

(Continued)

FOREIGN PATENT DOCUMENTS

JP 2002-336227 11/2002

*Primary Examiner*—Allen C. Ho
(74) *Attorney, Agent, or Firm*—Armstrong Teasdale LLP (57) ABSTRACT

A portable detector panel includes an X-ray detector assembly having an X-ray detecting surface on its surface, a box-like case that houses the X-ray detector assembly therein and whose upper part that is opposite to the X-ray detecting surface is X-ray transmissive, and a buffer member that is arranged between the inner side wall of the case and the X-ray detector assembly, is made of a hard material, and has a flexible shape with respect to the movement of the X-ray detector assembly in the direction generally parallel to the X-ray detecting surface.

20 Claims, 8 Drawing Sheets

U.S. PATENT DOCUMENTS

| | | | |
|---|---|---|---|
| 7,582,877 B2 * | 9/2009 | Dobrusskin et al. | 250/370.09 |
| 7,663,114 B2 * | 2/2010 | Aoyagi | 250/370.09 |
| 7,687,790 B2 * | 3/2010 | Utschig et al. | 250/515.1 |
| 2002/0150214 A1 | 10/2002 | Spahn | |

* cited by examiner

DETECTOR PANEL AND X-RAY IMAGING APPARATUS

CROSS REFERENCE TO RELATED APPLICATIONS

This application claims the benefit of Chinese Patent Application No. 200810074226.0 filed Feb. 13, 2008, which is hereby incorporated by reference in its entirety.

BACKGROUND OF THE INVENTION

The embodiments described herein relate to a detector panel and an X-ray imaging apparatus, and more particularly to a portable detector panel having an X-ray detector assembly housed in a case, and an X-ray imaging apparatus using such detector panel.

As a type of X-ray imaging apparatuses, there are mobile imaging apparatuses. The X-ray imaging apparatus of this type is composed of a movable system console and a portable detector panel. The system console includes an X-ray irradiator and a control circuit, while the detector panel is composed of an X-ray detector assembly and an X-ray transmissive flat case.

The X-ray imaging apparatus is carried to a hospital room of a patient for carrying out radiography. The radiography is carried out in the hospital room in such a manner that the detector panel is put on a part of the patient to be imaged, and an X-ray is irradiated from the opposite side. The X-ray signal detected by the detector panel is transmitted to the system console with wire or wirelessly (see, for example, Japanese Unexamined Patent Publication No. 2002-336227 (paragraph numbers 0017 to 0020, FIG. 1)).

The X-ray detector assembly includes an X-ray detector including a two-dimensional array of X-ray detecting elements that convert the incident X-ray into an electrical signal, a support substrate, an interface circuit, and a flexible circuit board that connects the X-ray detector and the interface circuit.

The two-dimensional array of the X-ray detecting elements is mounted to the surface of the support substrate, the interface circuit is mounted to the back surface of the support substrate, and the flexible circuit is mounted from the surface of the support substrate to the back surface.

The X-ray detector described above is rigidly fixed to the inner bottom wall of the case via a spacer made of an appropriate hard material, or fixed through a cushion that is made of a soft material and arranged below the spacer for absorbing impact (see, for example, U.S. Pat. No. 6,700,126 (columns 3 to 5, FIG. 4)).

BRIEF DESCRIPTION OF THE INVENTION

When the X-ray detector assembly is fixed in the case through the spacer made of a hard material, a shock produced when the detector panel is dropped on the floor and hit against something is directly transmitted, so that the X-ray detector assembly is susceptible to breakdown. When the cushion is arranged below the spacer, the shock to the X-ray detector assembly is eased, but there is a problem in the reliability of the cushion material.

Since the cushion is interposed, the precise positioning of the X-ray detector assembly becomes difficult, which brings poor productivity. Further, the stability of the X-ray detector assembly to the external environment is poor due to the temperature characteristic of the cushion or the affect by the external vibration.

In view of this, a detector panel is provided having shock resistance and excellent stability to the external environment, and an X-ray imaging apparatus that uses the detector panel.

In a first aspect, a portable detector panel includes an X-ray detector assembly having an X-ray detecting surface on its surface; a box-like case that houses the X-ray detector assembly therein and whose at least upper part that is opposite to the X-ray detecting surface is X-ray transmissive; and a buffer member that is arranged between the inner side wall of the case and the X-ray detector assembly, is made of a hard material, and has a flexible shape with respect to the movement of the X-ray detector assembly in the direction generally parallel to the X-ray detecting surface.

In a second aspect, the X-ray detector assembly includes: a support substrate; an X-ray detector supported on the upper surface of the support substrate; an electric circuit board supported on the lower surface of the support substrate; and a flexible circuit board that electrically connects the X-ray detector with the electric circuit.

In a third aspect, the detector panel also includes a spacer that supports the X-ray detector assembly housed in the case so as to be apart from the inner bottom wall of the case.

In a fourth aspect, the spacer is movable with respect to the movement of the X-ray detector assembly in the direction generally parallel to the X-ray detecting surface.

In a fifth aspect, the buffer member includes a beam arranged on the inner side wall of the case the X-ray detector assembly and is flexible with respect to the pressing force to the X-ray detector assembly in the direction generally parallel to the X-ray detecting surface.

In a sixth aspect, the beam are provided at four corners of the inner side wall of the case or the X-ray detector.

In a seventh aspect, the beam is a cantilever beam one end of which is supported on the inner side wall of the case or the X-ray detector assembly.

In an eighth aspect, the beam is in a shape corresponding to the shape of a corner of the X-ray detector assembly.

In a ninth aspect, the buffer member includes a beam that is arranged between the inner side wall of the case and the X-ray detector assembly and is flexible with respect to the pressing force to the X-ray detector assembly in the direction generally parallel to the X-ray detecting surface.

In a tenth aspect, the buffer member includes a straddle mounted beam that is arranged on a side face of the supporting substrate and is flexible with respect to the pressing force by a projecting portion arranged on an inner side wall of the case in the direction generally parallel to the X-ray detecting surface.

In an eleventh aspect, an X-ray imaging apparatus includes a system console having an X-ray irradiator and a control circuit; and a portable detector panel that detects an X-ray generated from the X-ray irradiator, the detector panel including: an X-ray detector assembly having an X-ray detecting surface on its surface; a box-like case that houses the X-ray detector assembly therein and whose at least upper part that is opposite to the X-ray detecting surface is X-ray transmissive; and a buffer member that is arranged between the inner side wall of the case and the X-ray detector assembly, is made of a hard material, and has a flexible shape with respect to the movement of the X-ray detector assembly in the direction generally parallel to the X-ray detecting surface.

In a twelfth aspect, the X-ray detector assembly includes: a support substrate; an X-ray detector supported on the upper surface of the support substrate; an electric circuit board supported on the lower surface of the support substrate; and a flexible circuit board that electrically connects the X-ray detector with the electric circuit.

In a thirteenth aspect, the detector panel further includes a spacer that supports the X-ray detector assembly housed in the case so as to be apart from the inner bottom wall of the case.

In a fourteenth aspect, the spacer is movable with respect to the movement of the X-ray detector assembly in the direction generally parallel to the X-ray detecting surface.

In a fifteenth aspect, the buffer member includes a beam arranged on the inner side wall of the case the X-ray detector assembly and is flexible with respect to the pressing force to the X-ray detector assembly in the direction generally parallel to the X-ray detecting surface.

In a sixteenth aspect, the beam are provided at four corners of the inner side wall of the case or the X-ray detector assembly.

In a seventeenth aspect, the beam is a cantilever beam one end of which is supported on the inner side wall of the case or the X-ray detector assembly.

In an eighteenth aspect, the beam is in a shape corresponding to the shape of a corner of the X-ray detector assembly.

In a nineteenth aspect, the buffer member includes a beam that is arranged between the inner side wall of the case and the X-ray detector assembly and is flexible with respect to the pressing force to the X-ray detector assembly in the direction generally parallel to the X-ray detecting surface.

In a twentieth aspect, the buffer member includes a straddle mounted beam that is arranged on a side face of the supporting substrate and is flexible with respect to the pressing force by a projecting portion arranged on an inner wall of the case in the direction generally parallel to the X-ray detecting surface.

In some embodiments, the detector panel includes a buffer member that is arranged between the inner side wall of the case and the X-ray detector assembly, is made of a hard material, and has a flexible shape with respect to the movement of the X-ray detector assembly in the direction generally parallel to the X-ray detecting surface. Therefore, the detector panel facilitates shock resistance and excellent stability with respect to the external environment.

DETAILED DESCRIPTION OF THE INVENTION

Figure 1:
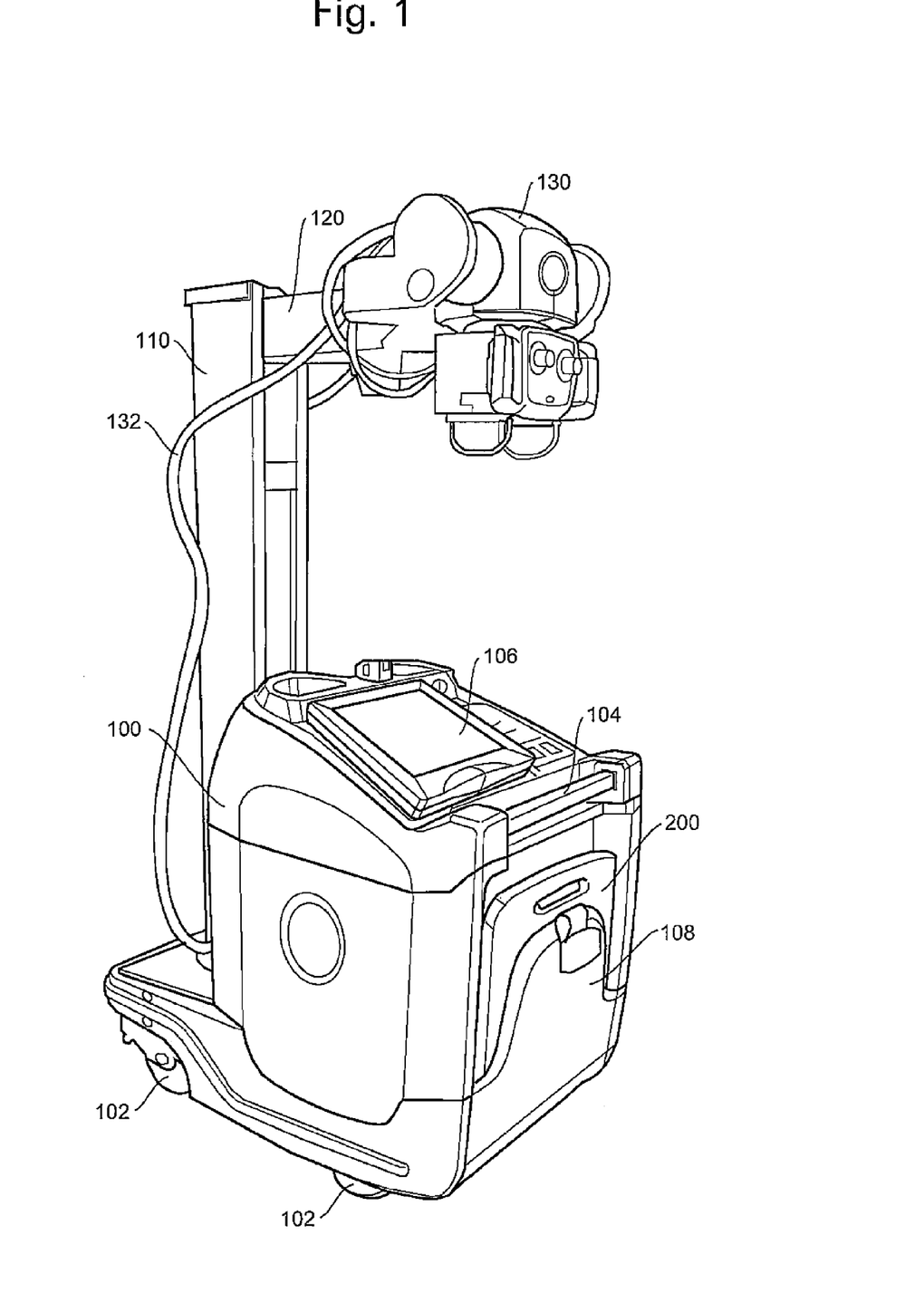
FIG. 1 is a view showing an appearance of an exemplary X-ray imaging apparatus.

Various embodiments of the present invention will be explained in detail with reference to the drawings. The present invention is not limited to the embodiments described herein. FIG. 1 schematically shows the appearance of an X-ray imaging apparatus. The configuration of this apparatus represents only one example of the X-ray imaging apparatus.

Figure 2:
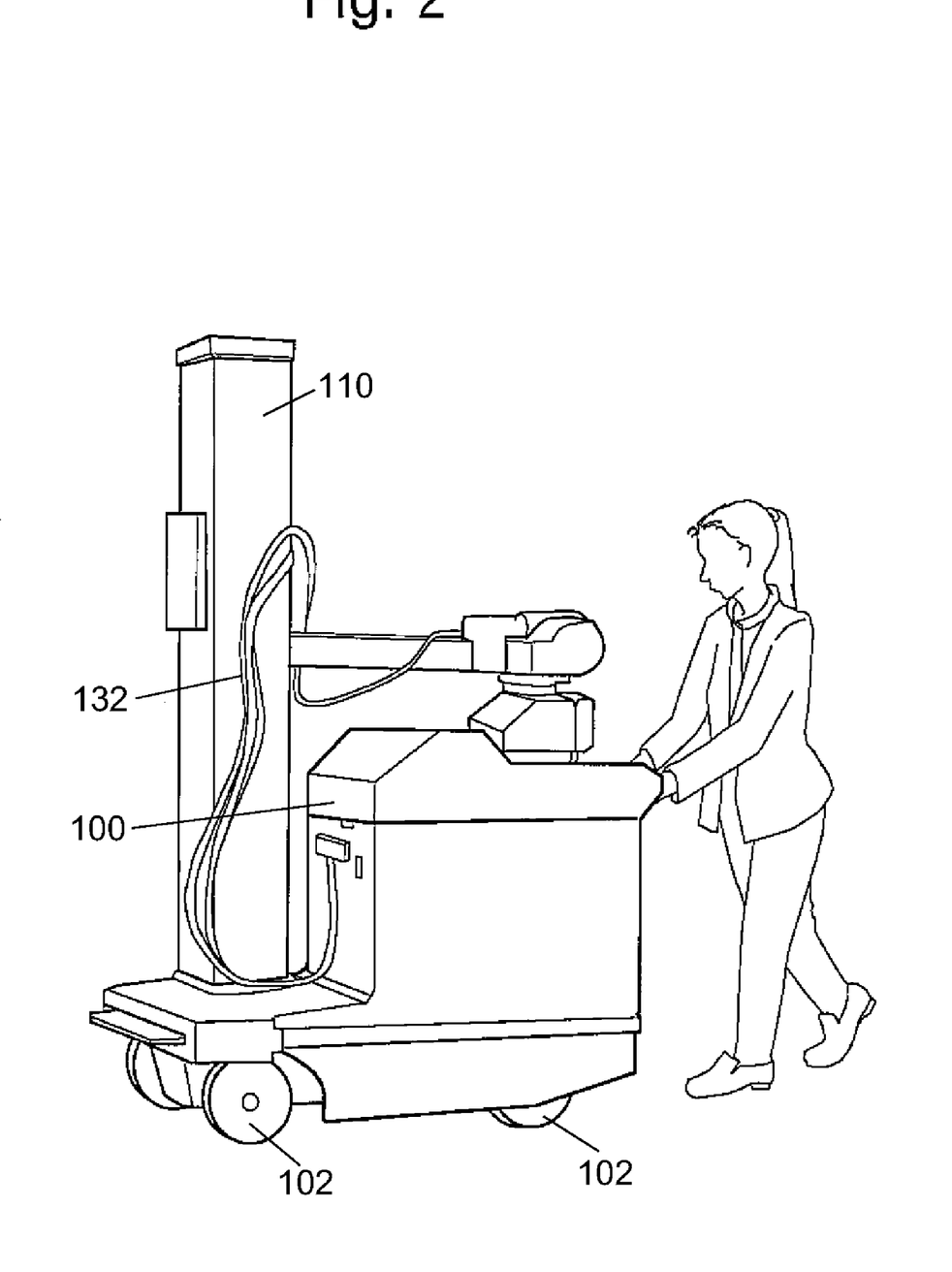
FIG. 2 is a view showing the state in which the X-ray imaging apparatus shown in FIG. 1 is being moved.

As shown in FIG. 1, the present apparatus has a system console 100. The system console 100 has a box-like structure of substantially a rectangular solid, and has an electric circuit for imaging control in its inside. The system console 100 has a caster 102 for movement at its lower part and a grip handle 104 at its upper part. Thus, the present apparatus becomes a movable X-ray imaging apparatus that can be freely moved as shown in FIG. 2.

An operation panel 106 is provided to the upper surface of the system console 100. The operation panel 106 includes a man-machine communication device such as, for example, a graphic display or a keyboard.

A vertical column 110 is provided to the back of the system console 100. An X-ray irradiator 130 is mounted to a leading end of an arm 120 that extends horizontally from the column 110. The X-ray irradiator 130 generates X-ray by a high voltage supplied from the system console 100 through a cable 132.

The direction of the X-ray irradiator 130 is changeable at the leading end of the arm 120. The arm 120 can be moved up and down along the column 110. The column 110 is spinnable about the longitudinal shaft.

The present apparatus has a detector panel 200. The detector panel 200 has a plate-like structure of substantially a rectangular shape. It is provided separate from the system console 100, and is portable. The detector panel 200 is stored in a bin 108 at the front of the system console 100 when radiography is not carried out. When the radiography is carried out, the detector panel 200 is take out of the bin 108 for use. The detector panel 200 is one example of a best mode for carrying out the present invention. The configuration of the detector panel 200 illustrates one example of the best mode for carrying out the present invention relating to a detector panel.

Figure 3:
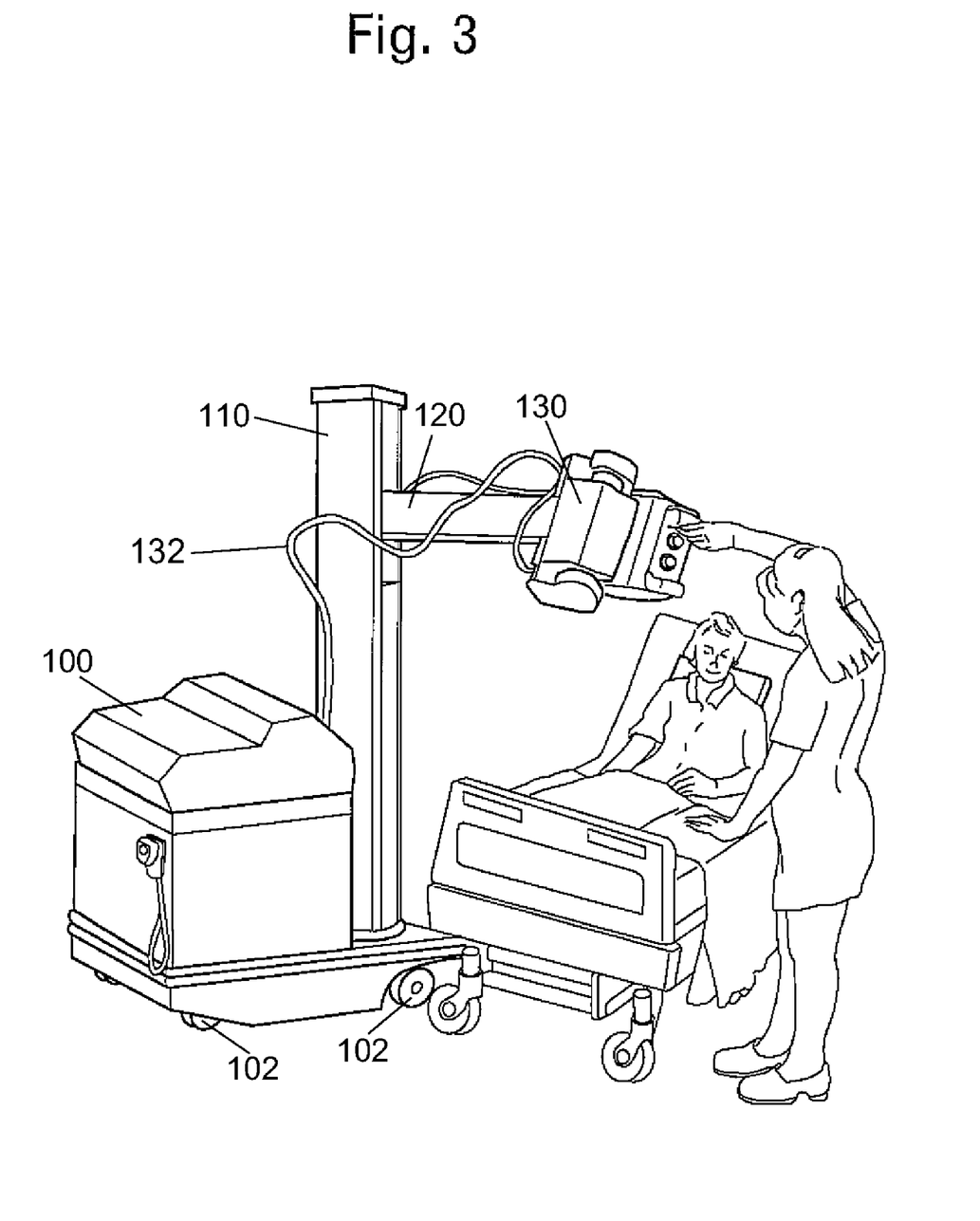
FIG. 3 is a view showing the state in which a patient is imaged by the X-ray imaging apparatus shown in FIG. 1.

FIG. 3 shows the scene when the present apparatus is used. As shown in FIG. 3, the present apparatus is used in a hospital room. Radiography is carried out in such a manner that the detector panel 200 is put on the back of a patient, and X-ray is irradiated from the front side by the X-ray irradiator 130 of the system console 100. The X-ray signal detected by the detector panel 200 is transmitted wirelessly or by a cable (not shown) to the system console 100.

Figure 4:
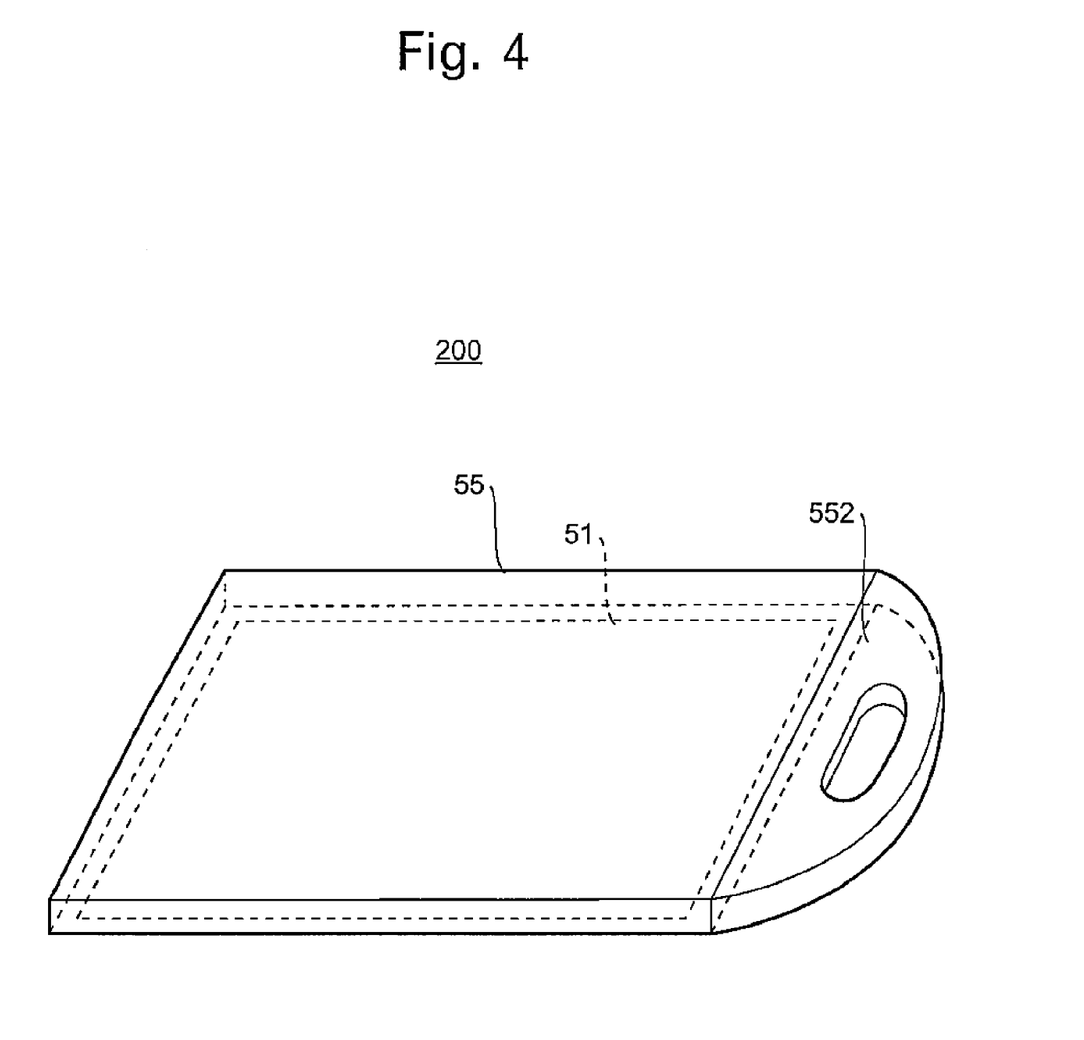
FIG. 4 is a view showing a basic configuration of a detector panel that may be used with the X-ray imaging apparatus shown in FIG. 1.

FIG. 4 shows a basic configuration of the detector panel 200. As shown in FIG. 4, the detector panel 200 has a box-like case 55 and a rectangular plate-like X-ray detector assembly 51 housed in the case 55. The upper part of the case 55 that is opposite to an X-ray detecting surface 52a' of the X-ray detector assembly 51 is made of an X-ray transmissive material. The case 55 has a grip 552 at its one end.

Figure 5:
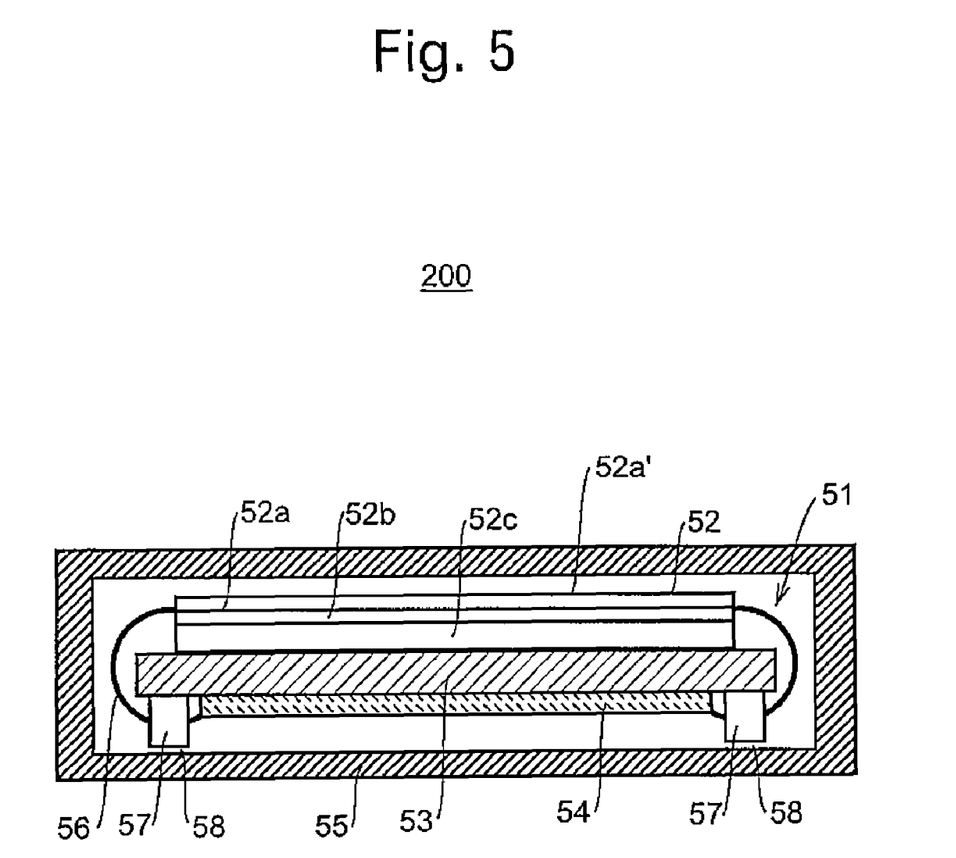
FIG. 5 is a view showing a basic internal configuration of the detector panel shown in FIG. 4.

FIG. 5 shows one example of an internal configuration of the detector panel 200. FIG. 5 is a vertical sectional view of the detector panel 200. As shown in FIG. 5, the X-ray detector assembly 51 is composed of an X-ray detector 52, a support substrate 53, and an electronic circuit board 54. The X-ray detector 52 is mounted to the surface of the support substrate 53, and the electronic circuit board 54 is mounted to the back surface of the support substrate 53, wherein both are electrically connected by a flexible circuit board 56.

The X-ray detector 52 is constructed by laminating a scintillator layer 52a and a photoelectric conversion layer 52b over a glass substrate 52c. The scintillator layer 52a converts X-rays into light, and the photoelectric conversion layer 52b converts this light into an electrical signal. The photoelectric conversion layer 52b is constructed of a two-dimensional array of such photoelectric conversion elements as photodiodes. The electrical signal obtained as the result of conversion is inputted to the electric circuit board 54 through the flexible circuit board 56.

An electric circuit is mounted to the electric circuit board 54. The electric circuit is an interface to the system console 100. It converts the inputted signal into digital data and transmits the resultant to the system console 100 wirelessly or by a cable (not shown).

The rear face of the support member 53 is provided with a plurality of spacers 57. The support member 53 is kept at a distance from the inner bottom wall of the case 55 by the spacers 57. The end faces 58 of the spacers 57 are not fixed on the inner bottom wall of the case 55. That is, the end faces 58 of the spacers 57 are moving ends. The spacers 57 may be provided on the case 55 side. In this case, the end faces on the support member 53 side are moving ends.

Figure 6:
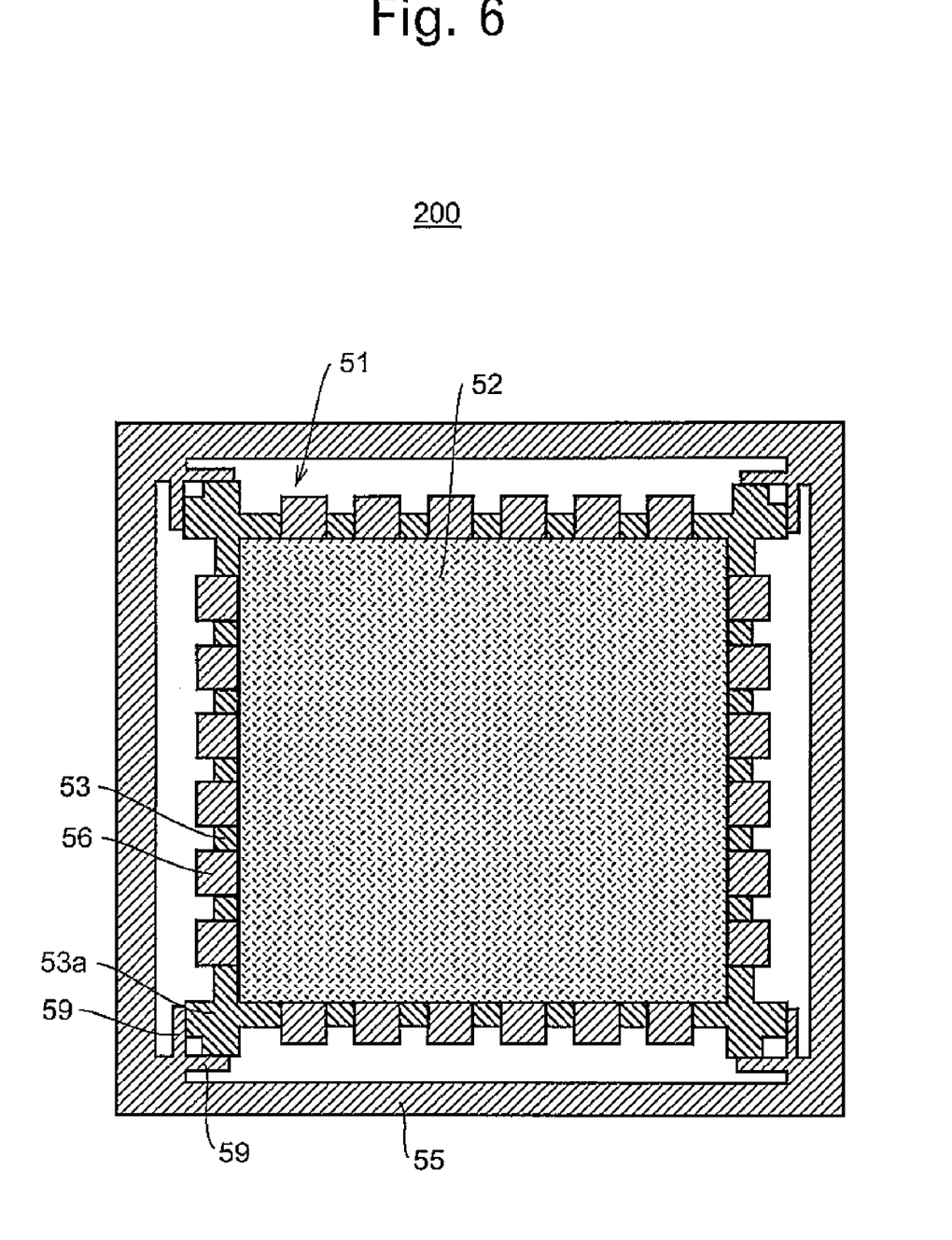
FIG. 6 is a horizontal sectional view showing a basic configuration of the detector panel shown in FIG. 4.

FIG. 6 illustrates an example of the internal configuration of the detector panel 200 in the form of horizontal sectional view. As illustrated in FIG. 6, the case 55 has a buffer member 59 at each of the four corners of its inner circumferential surface. The buffer members 59 are each constructed of a pair of cantilever beams having a flexible structure in the direction of bending. Each pair of cantilever beams has an opening angle of 90 degrees at a cantilever portion.

The flexible shape here means the shape that functions as a rigid body with respect to a shock or vibration produced upon a normal use, and that functions as an elastic body so as to absorb energy with respect to an extreme shock or vibration applied when dropped on a floor or hit against something. The buffer members described above can be realized by appropriately designing the material, shape and size. The buffer members 59 are constructed integrally with the case 55. These buffer members 59 are constructed, for example, by molding the case 55 integrally with the buffer members 59.

The support member 53 has a projecting portion 53*a* at each of its four corners in correspondence with these buffer members 59. The four projecting portions 53*a* are respectively abutted against the four buffer members 59. Each portion constructed of a buffer member 59 and a protruded portion 53*a* is an example of a supporting mechanism of the invention.

When excessive impact or vibration is horizontally applied, the buffer members 59 perform buffering action by flexing their beams. Impact or vibration is horizontally applied when a corner or an edge of the detector panel 200 hits the floor or a foreign object or on any other like occasion. Impact and like on the X-ray detector assembly 51 is lessened by the buffer members, and the X-ray detector assembly 51 becomes less prone to fail. In addition, a cushion material or the like is not used for buffering, and high reliability is obtained.

Figure 7:
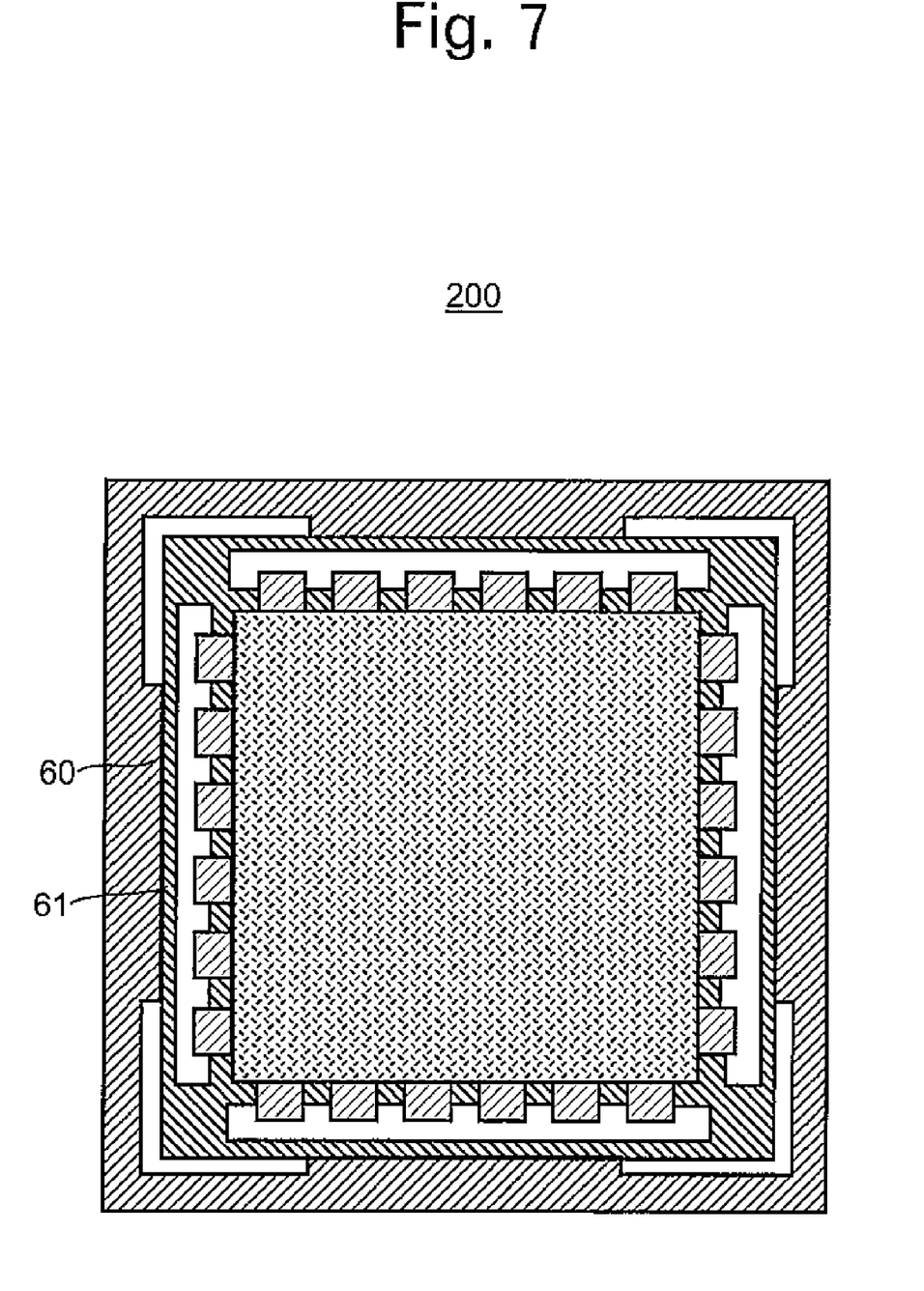
FIG. 7 is a horizontal sectional view showing another basic configuration of the detector panel shown in FIG. 4.

FIG. 7 illustrates another example of the internal configuration of the detector panel 200 in the form of horizontal sectional view. As illustrated in FIG. 7, the case 55 has four projecting portions 60 on its inner circumferential surface on four sides. The support member 53 has a buffer member 61 on its four side in correspondence with these protruded portions 60. The four buffer members 61 are abutted against the four respective protruded portions 60. The buffer members 61 are each constructed of a straddle mounted beam flexible when horizontally pressed by the X-ray detector assembly 51. The buffer members 61 are constructed integrally with the support member 53. These buffer members 61 are constructed, for example, by molding the support member 53 integrally with the buffer members 61.

When excessive impact or vibration is horizontally applied, the buffer members 61 perform buffering action by flexing their beams. This lessens impact or the like on the X-ray detector assembly 51, and the X-ray detector assembly 51 becomes less prone to fail. In addition, a cushion material or the like is not used for buffering, and high reliability is obtained.

Figure 8:
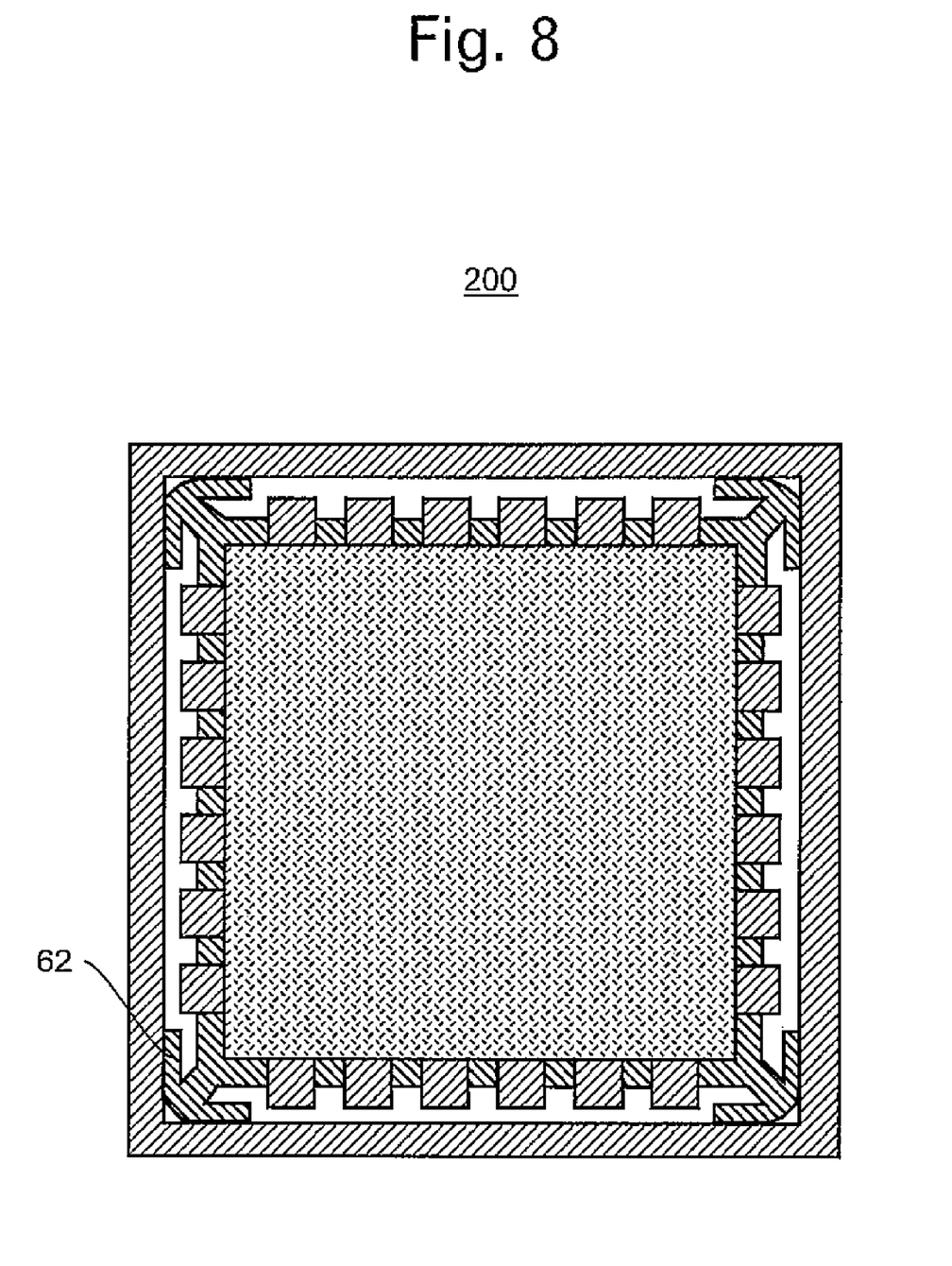
FIG. 8 is a horizontal sectional view showing another basic configuration of the detector panel shown in FIG. 4.

FIG. 8 illustrates another example of the internal configuration of the detector panel 200 in the form of horizontal sectional view. As illustrated in FIG. 8, the support member 53 has buffer members 62 respectively formed at its four corners. The buffer members 62 are diagonally extended from the four corners. Their ends are each constructed of a beam abutted against the corresponding one of the four corners on the inner circumference of the case 55. The beams are in such a shape that they are flexible under pressing force horizontally applied to the X-ray assembly 51.

The buffer members 62 are constructed integrally with the support member 53. These buffer members 62 are constructed, for example, by molding the support member 53 integrally with the buffer members 62. When excessive impact or vibration is horizontally applied, the buffer members 62 perform buffering action by flexing their beams. This lessens impact or the like on the X-ray detector assembly 51, and the X-ray detector assembly 51 becomes less prone to fail. In addition, a cushion material or the like is not used for buffering, and high reliability is obtained.

What the claimed is:

1. A portable detector panel comprising:
   an X-ray detector assembly comprising an X-ray detecting surface;
   a box-like case configured to house said X-ray detector assembly therein and comprising an X-ray transmissive upper part positioned opposite said X-ray detecting surface; and
   a buffer member arranged between an inner side wall of said case and said X-ray detector assembly, said buffer member composed of a hard material, integrally formed with one of said X-ray detector assembly and said case, and having a flexible shape with respect to movement of said X-ray detector assembly in a direction generally parallel to said X-ray detecting surface.

2. The portable detector panel according to claim 1, wherein said X-ray detector assembly further comprises:
   a support substrate;
   an X-ray detector supported on an upper surface of said support substrate;
   an electric circuit board supported on a lower surface of said support substrate; and
   a flexible circuit board configured to electrically connect said X-ray detector and said electric circuit board.

3. The portable detector panel according to claim 1, further comprising:
   a spacer configured to support said X-ray detector assembly and positioned apart from an inner bottom wall of said case.

4. The portable detector panel according to claim 3, wherein:
   said spacer is movable with respect to the movement of said X-ray detector assembly in the direction generally parallel to said X-ray detecting surface.

5. The portable detector panel according to claim 1, wherein:
   said buffer member comprises a beam arranged on said inner side wall of said case and flexible with respect to a pressing force imparted on said X-ray detector assembly in the direction generally parallel to said X-ray detecting surface.

6. The portable detector panel according to claim 5, wherein:
said beam comprises a plurality of beams, each beam provided at a corner of one of said inner side wall of said case and said X-ray detector assembly.

7. The portable detector panel according to claim 5, wherein:
said beam comprises a cantilever beam, a first end of said cantilever beam is supported on one of said inner side wall of said case and said X-ray detector assembly.

8. The portable detector panel according to claim 5, wherein:
said beam is in a shape corresponding to a shape of a corner of said X-ray detector assembly.

9. The portable detector panel according to claim 1, wherein:
said buffer member comprises a beam that is arranged between said inner side wall of said case and said X-ray detector assembly and is flexible with respect to a pressing force imparted on said X-ray detector assembly in the direction generally parallel to said X-ray detecting surface.

10. The portable detector panel according to claim 9, wherein:
said X-ray detector further comprises a support substrate; and
said beam comprises a straddle mounted beam that is arranged on a side face of said support substrate and is flexible with respect to the pressing force by a projecting portion arranged on said inner side wall of said case in the direction generally parallel to said X-ray detecting surface.

11. An X-ray imaging apparatus comprising:
a system console comprising an X-ray irradiator and a control circuit; and
a portable detector panel configured to detect an X-ray generated from said X-ray irradiator, said detector panel comprising:
an X-ray detector assembly comprising an X-ray detecting surface;
a box-like case configured to house said X-ray detector assembly therein and comprising an X-ray transmissive upper part positioned opposite to said X-ray detecting surface; and
a buffer member arranged between an inner side wall of said case and said X-ray detector assembly, said buffer member composed of a hard material, integrally formed with one of said X-ray detector assembly and said case, and having a flexible shape with respect to movement of said X-ray detector assembly in a direction generally parallel to said X-ray detecting surface.

12. The X-ray imaging apparatus according to claim 11, wherein:
said X-ray detector assembly further comprises:
a support substrate;
an X-ray detector supported on an upper surface of said support substrate;
an electric circuit board supported on a lower surface of said support substrate; and
a flexible circuit board configured to electrically connect said X-ray detector and said electric circuit board.

13. The X-ray imaging apparatus according to claim 11, wherein:
said detector panel further comprises a spacer configured to support said X-ray detector assembly and positioned apart from an inner bottom wall of said case.

14. The X-ray imaging apparatus according to claim 13, wherein:
said spacer is movable with respect to the movement of said X-ray detector assembly in the direction generally parallel to said X-ray detecting surface.

15. The X-ray imaging apparatus according to claim 11, wherein:
said buffer member comprises a beam arranged on said inner side wall of said case, said beam is flexible with respect to a pressing force imparted on said X-ray detector assembly in the direction generally parallel to said X-ray detecting surface.

16. The X-ray imaging apparatus according to claim 15, wherein:
said beam comprises a plurality of beams, each beam positioned at a corner of one of said inner side wall of said case and said X-ray detector assembly.

17. The X-ray imaging apparatus according to claim 15, wherein:
said beam comprises a cantilever beam, a first end of said beam is supported on one of said inner side wall of said case and said X-ray detector assembly.

18. The X-ray imaging apparatus according to claim 15, wherein:
said beam is in a shape corresponding to a shape of a corner of said X-ray detector assembly.

19. The X-ray imaging apparatus according to claim 11, wherein:
said buffer member comprises a beam that is arranged between said inner side wall of said case and said X-ray detector assembly and is flexible with respect to a pressing force imparted on said X-ray detector assembly in the direction generally parallel to said X-ray detecting surface.

20. The X-ray imaging apparatus according to claim 19, wherein:
said X-ray detector assembly further comprises a support substrate; and
said beam comprises a straddle mounted beam arranged on a side face of a support substrate and is flexible with respect to the pressing force by a projecting portion arranged on said inner wall of said case in the direction generally parallel to said X-ray detecting surface.

* * * * *